United States Patent [19]
Johns

[11] Patent Number: 5,733,251
[45] Date of Patent: Mar. 31, 1998

[54] POP TOP DRESSING APPLICATOR

[75] Inventor: Owen L. Johns, Madeira Beach, Fla.

[73] Assignee: Medical Device Designs, Inc., Clearwater, Fla.

[21] Appl. No.: 700,260

[22] Filed: Aug. 20, 1996

[51] Int. Cl.⁶ .......................................... A61F 5/00
[52] U.S. Cl. .................. 602/57; 602/52; 602/54; 602/58
[58] Field of Search ................ 602/41–59; 128/888, 128/889; 604/304, 305, 306, 307

[56] References Cited

U.S. PATENT DOCUMENTS

| | | |
|---|---|---|
| 2,469,064 | 5/1949 | Campbell . |
| 2,572,641 | 10/1951 | Manley . |
| 2,721,550 | 10/1955 | Banff . |
| 2,969,057 | 1/1961 | Simmons . |
| 3,416,524 | 12/1968 | Meier . |
| 3,872,862 | 3/1975 | Hume . |
| 3,888,247 | 6/1975 | Stenvall . |
| 3,903,882 | 9/1975 | Auqurt . |
| 4,265,234 | 5/1981 | Schaar . |
| 4,513,739 | 4/1985 | Johns . |
| 4,545,371 | 10/1985 | Grossman et al. . |
| 4,545,372 | 10/1985 | Lauritzen . |
| 4,549,653 | 10/1985 | Lauritzen . |
| 4,598,004 | 7/1986 | Heinecke . |
| 4,600,001 | 7/1986 | Gilman . |
| 4,614,183 | 9/1986 | McCracken et al. . |
| 4,641,643 | 2/1987 | Greer . |
| 4,664,106 | 5/1987 | Snedeker . |
| 4,743,232 | 5/1988 | Kruger . |
| 4,781,293 | 11/1988 | Johns . |
| 4,787,380 | 11/1988 | Scott ........................... 206/441 |
| 4,815,457 | 3/1989 | Manars et al. . |
| 4,915,102 | 4/1990 | Kwiatek et al. . |
| 4,915,227 | 4/1990 | Johns . |
| 4,915,228 | 4/1990 | Johns . |
| 4,928,680 | 5/1990 | Sandbank . |
| 5,035,687 | 7/1991 | Sandbank . |
| 5,099,832 | 3/1992 | Ward . |

*Primary Examiner*—Richard J. Apley
*Assistant Examiner*—Kim M. Lee
*Attorney, Agent, or Firm*—Joseph C. Mason, Jr.

[57] ABSTRACT

An improved medical dressing, including a dressing layer having a first face and a second face, the first face having an adhesive coating on at least a portion thereof; a release layer covering the dressing layer in releasable contact with the adhesive face of the dressing layer; a support layer covering the dressing layer in releasable contact with the second face of the dressing layer, the dressing layer having smaller surface dimension than the release layer and the support letter, the support layer having on at least one side thereof a U-shaped perforation therethrough, the perforation extending from an area adjacent an edge of the support layer and overlapping the smaller surface dimension of the dressing layer; and a delivery means for applying the dressing layer to a wound site, the delivery means pivotally mounted on a portion of the support layer adjacent the base of the U-shaped perforation.

10 Claims, 4 Drawing Sheets

POP TOP DRESSING APPLICATOR

FIELD OF THE INVENTION

This invention relates, generally, to an improved medical dressing for protecting external wounds of mammals, especially humans. More particularly, it relates to an external wound dressing having a pressure sensitive adhesive portion which is easily applied to a wound site.

BACKGROUND OF THE INVENTION

Numerous dressings have been developed for the protection of both accidental wounds such as burns and abrasions and for the protection of deliberate cuts to the skin such as surgical incisions and medical device insertion sites. In addition, a variety of dressings have been developed for the protection and treatment of dermatological disorders. Many of these dressings are selectively permeable to oxygen and water vapor while being impervious to liquids, infectious microorganisms and body salts. It is also known that wound dressings can contain an absorbent pad material surrounded at the periphery by a pressure sensitive adhesive portion which holds the dressing in place. Other known dressings are simply pressure sensitive adhesive sheets which may or may not be used in conjunction with a sterile gauze or other sterile absorbent material.

Prior art wound dressings are oftentimes quite complex and require multiple layers in order to maintain sterility and ensure proper application of the dressing. One of the layers, the film or gauze layer is called the dressing layer. The dressing layer can be made entirely of an adhesive coated film, or can include an adhesive coating around the periphery of an absorbent material.

A second layer, the release layer, may be releasably secured to the adhesive surface of the dressing layer. The release layer can be in one or more pieces and prevents the adhesive surface of the dressing layer from sticking to anything prior to removal of the release layer. Further, the release layer facilitates the maintenance of the sterility of the dressing layer. The maintenance of sterility during the removal of the release layer is critical. Specifically, it is important that as the release layer is removed, there is no contamination of the dressing layer, particularly its underside.

Some wound dressings also include a third layer. This third layer is sometimes referred to as a support layer. Occasionally, the wound dressing is manufactured on the support layer.

The use of multi-layer wound dressings complicates application of a dressing to a wound site. Since these dressings usually have some portion which contains at least one adhesive surface, a critical range of relative coefficients of adhesion between the layers is required for proper application to the wound site. Specifically, each layer of the dressing has a specific strength or coefficient of adhesion relative to each of the other layers of the dressing.

The strength of the adhesive bond between the layers must be within a critical range for the prior art dressings to function properly. If the coefficient of adhesion for any one of the layers is improper relative to any other layer, the health care provider will be either unable to access or apply the dressing. In particular, if the adhesive bond is too weak between the support layer and the dressing layer, the dressing layer will be separated from the support layer when the release layer is removed. Alternatively, if the adhesive bond is too strong between the support layer and the dressing layer, the dressing layer will be dislodged from the wound site when the support layer is removed.

To facilitate the separation of the layers in the proper sequence, the release layer may consist of several pieces. Multiple release layer pieces are problematic since they must be removed in a particular sequence and cause an additional problem of multiple articles of waste. If the dressing is accessed improperly the risk of contamination of the dressing and/or the wound site is greatly increased. In addition, improper access of the dressing may also result in improper application of the dressing to the wound site or the inability to apply the dressing to the wound site due to the adhesive surface of the dressing adhering to itself or another inappropriate surface, such as the rubber gloves of a health care provider.

Different variations, combinations and sizes of pressure sensitive adhesive dressings with or without an absorbent pad material have been developed over the years. Numerous approaches, having varying degrees of success, have attempted to overcome the deficiencies in the prior art multiple layer dressings. Specifically, various wound dressings have employed packaged systems, for example, U.S. Pat. Nos. 4,781,293, 4,915,227 and 4,915,228 to Johns, U.S. Pat. No. 4,743,232 to Kruger, U.S. Pat. Nos. 4,545,372 and 4,549,653 to Lauritzen and U.S. Pat. No. 5,099,832 to Ward. Wound dressings have also employed numerous applicators, for example, U.S. Pat. No. 4,928,680 to Sandbank, U.S. Pat. No. 4,598,004 to Heinecke, U.S. Pat. No. 4,915,102 to Kwiatek et al. and U.S. Pat. No. 4,545,371 to Grossmann et al. Other wound dressings have attempted to solve the prior art problems by using multi-layer dressings requiring varying degrees of force to separate the layers, for example, U.S. Pat. No. 4,513,739, to Johns, U.S. Pat. No. 5,035,687 to Sandbank, U.S. Pat. No. 4,815,457 to Mazars et al., U.S. Pat. No. 4,600,001 to Gilman, U.S. Pat. No. 4,664,106 to Snedeker, U.S. Pat. No. 4,265,234 to Schaar, U.S. Pat. No. 4,614,183 to McCracken et al. and U.S. Pat. No. 4,641,643 to Greer.

However, all of these dressings are easily wrinkled, require critical ranges of coefficients of adhesion and/or supporting handles, frames or sheets to aid in the application of the dressing to the wound site.

In view of the prior art at the time the present invention was made, it was not obvious to those of ordinary skill in the pertinent art how the needed wound dressing could be provided.

SUMMARY OF THE INVENTION

In accordance with the present invention, a medical dressing comprising a dressing layer having a first face and a second face, the first face having an adhesive coating on at least a portion thereof; a release layer covering the dressing layer in releasable contact with the adhesive face of the dressing layer; a support layer covering the dressing layer in releasable contact with the second face of the dressing layer, the dressing layer having smaller surface dimension than the release layer and the support letter, the support layer having on at least one side thereof a U-shaped perforation therethrough, the perforation extending from an area adjacent an edge of the support layer and overlapping the smaller surface dimension of the dressing layer; and a delivery means for applying the dressing layer to a wound site during removal of the support layer, the delivery means pivotally mounted on a portion of the support layer adjacent the base of the U-shaped perforation is disclosed.

The present invention also discloses a medical dressing, comprising a dressing layer having a first face and a second face, the first face having an adhesive coating on at least a portion thereof; a release layer covering the dressing layer in releasable contact with the adhesive face of the dressing layer; a support layer covering the dressing layer in releasable contact with the second face of the dressing layer, the dressing layer having smaller surface dimension than the release layer and the support letter, the support layer having on at least one side thereof a U-shaped perforation therethrough, the perforation extending from an area adjacent an edge of the support layer and overlapping the smaller surface dimension of the dressing layer; and a delivery means for applying the dressing layer to a wound site, the delivery means pivotally mounted on a portion of the support layer adjacent the base of the U-shaped perforation.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE INVENTION

Figure 1:
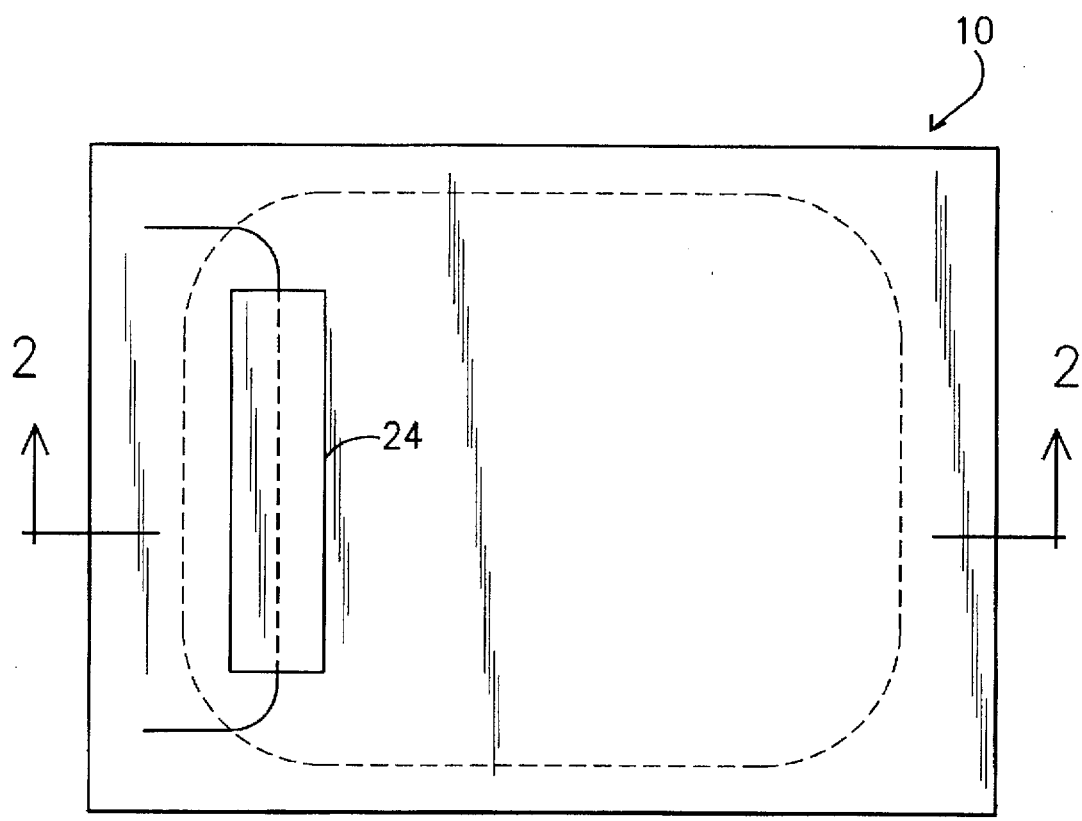
FIG. 1 is a top plan view of a wound dressing of the present invention.

Referring now to the drawings, in which like numerals refer to like elements thereof, FIG. 1, shows an embodiment of the invention which is denoted as a whole by the reference numeral 10.

Figure 2:
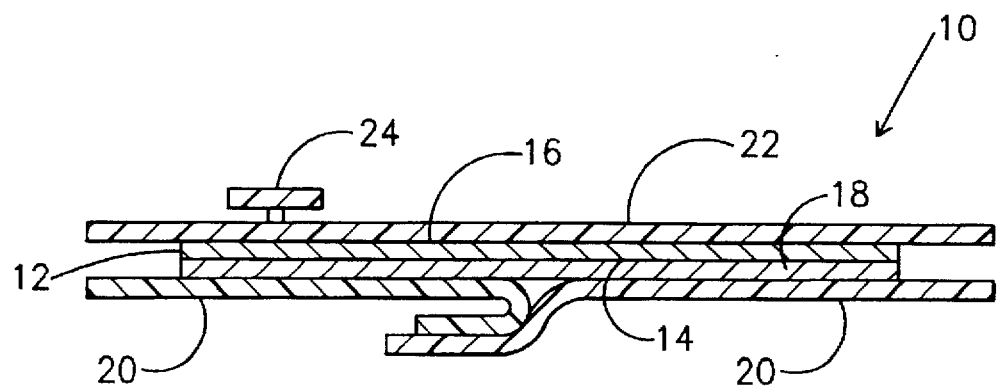
FIG. 2 is a side, cross-sectional view of the wound dressing shown in FIG. 1, taken along lines 2—2 thereof.

FIG. 2 is a side, cross-sectional view of the wound dressing shown in FIG. 1, taken along lines 2—2 thereof. As shown in FIG. 2 wound dressing 10 is a composite structure in which a dressing layer 12 is applied to a wound site. The dressing layer 12 may consist of a moisture vapor permeable film made from synthetic polymers which are capable of being formed into continuous films by casting, extrusion or other known film making processes. The dressing layer 12 has on one side thereof a first face 14 which is at least partially coated with an adhesive 18 and a second face 16 on an opposite side thereof. Preferred films of dressing layer 12 are permeable to moisture and vapor and should transmit moisture vapor. When a high moisture vapor permeable film is used the adhesive used is preferably biocompatible.

Suitable films, adhesives and their preparations are described, for example, in U.S. Pat. No. 3,645,835, which is incorporated herein by reference. These adhesive coated films should preferably have a water vapor transmission rate (WVTR) of at least 250 g/m$^2$/24 hrs (40° C., 80% relative humidity (RH)). Especially preferred are such adhesive coated films with a WVTR of about 400 to 500 g/m$^2$/24 hrs in which the backing material is a transparent polyurethane film having a thickness of about 0.5 to 2 mils (13 to 51 microns) and coated with a 1 mil (25 microns) layer of pressure-sensitive acrylic ester copolymer adhesive.

The film is also preferably conformable to body surfaces. Conformability is somewhat dependent on thickness, thus the thinner the film the more conformable it is. In a preferred embodiment the film thickness is from 0.5 to 5 mils. Further, the film may be continuous in that is has no perforations or pores in the body contacting portion of the film. In addition, the film may be a gauze, a nonwoven material or of a perforated film as the medical application may require. Films of this type are known in the art and generally are hydrophilic, polymeric materials such as polyether block amides, copolymers of cyclic polyesters, elastomeric polyesters, blends of polyurethane and polyester, chlorinated polyethylene, styrene/butadiene block copolymers, polyvinyl chloride and other commercial polyurethane compositions. Nonwoven sheet materials with pore diameters below twenty (20) microns are useful in the present invention. Alternatively, films coated on one face with a thin bacteria proof layer of polymer can also be used.

The adhesive 18 deposed on the first face 14 of dressing layer 12 may be selected from any number of commercially available medical grade adhesives known in the art. For example, multipolymer emulsions comprising stable pressure-sensitive aqueous acrylic adhesives having a solids content of 59% and a viscosity of 1,500-Z, 300 CPS are useful in the present invention. The adhesive properties of medical grade adhesives can be adjusted by the addition of a greater amount of crosslinking additives and/or by utilizing different coating weights and/or viscosities of the adhesive materials.

The dressing layer 12 is a material which would be extremely difficult, if not impossible, to handle by itself if not for the support and occlusion of one or more areas of the adhesive 18 on first face 14, which is provided by release layer 20. The necessity of wearing latex gloves, for the protection of both the patient and the caregiver, totally precludes contact with the adhesive surface 18 of the dressing layer 12 during dressing application. If contact should occur the adhesive surface 18 of dressing layer 12 will adhere to the stretchy gloves. This contact may result in contamination or waste of dressing layer 12.

Adhesive surface 18 of dressing layer 12 is protected from contact, until application to a wound site, by release layer 20. Release layer 20 is oriented coplanarly adjacent to and releasably secured to the adhesive surface 18 of the first face 14 of dressing layer 12. Release layer 20 may be made of any relatively stiff sheet material such as paper, polyethylene or polypropylene which will adequately protect dressing layer 12 and be properly released from adhesive surface 18. Specifically, release layer 20 can be made from numerous commercially available silicone or teflon coated release sheets known in the art. Base polymers and papers, such as polyester, polypropylene, polyethylene, styrene, unbleached and bleached kraft papers which can be clay coated or uncoated are also useful in the present invention. Numerous materials known in the art would be suitable based on factors including the need for transparency, stiffness and release force from a chosen adhesive. Additionally, release layer 20 can be made of polyethylene, polypropylene or polyester which is coated with a releasing agent such as silicone or fluorochemicals. Preferred release layers are silicone coated.

Wound dressing 10 further includes a support layer 22. Support layer 22 has a delivery means 24 for application of the wound dressing layer 12 to a wound site. Support layer 22 is oriented coplanarly adjacent to and releasably secured to the second face 16 of dressing layer 12. Support layer 22 and release layer 20 have dressing layer 12 sandwiched therebetween, preferably centrally disposed.

Delivery means 24 is pivotally mounted on a portion of support layer 22. Delivery means 24 facilitates application of dressing layer 12 to a wound site. Delivery means 24 may be integral with support layer 22. Delivery means 24 causes a portion of support layer 22 to force dressing layer 12 away from the plane of support layer 22. Specifically, delivery means 24 includes a portion of support layer 22 which declines away from a plane of support layer 22 in such a manner that dressing layer 12 is forced away from support layer 22 during removal of support layer 22 from dressing layer 12 thereby applying dressing layer 12 to the wound site. In particular, delivery means 24 may be a hinged mechanism such as a hinged handle similar to a pop top device such as those used to open beverage cans. Application of dressing layer 12 is effected by movement of a hinged member of delivery means 24 from a parallel position to a perpendicular position relative to support layer 22. This movement to a perpendicular position causes a portion of support layer 22 to force dressing layer 12 away from the plane of support layer 22 during removal of support layer 22. In this way, by freeing the edge of dressing layer 12 to adhere to the patient and start separation of support layer 22, the present invention solves the problem of the prior art devices which require critical ranges in the relative coefficients of adhesion of composite dressings.

Figure 3:
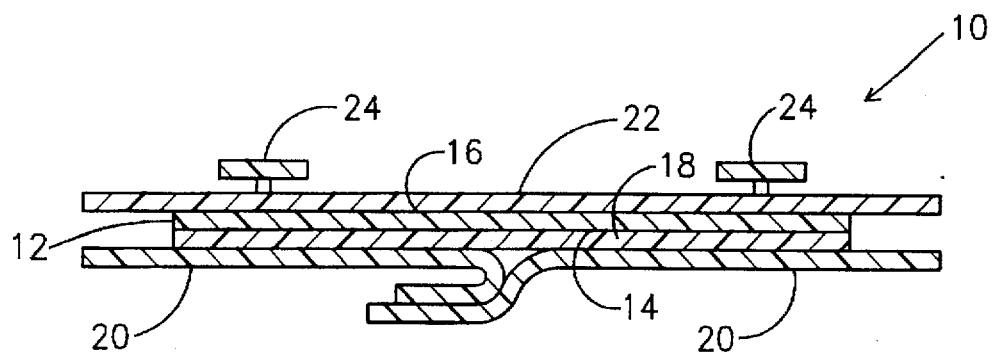
FIG. 3 is a side cross-sectional view of another wound dressing according to the present invention.

FIG. 3 is a further embodiment of the present invention. FIG. 3 is similar to FIG. 2 in all material respects except that the health care provider can use one or both of the delivery means 24 for application of dressing layer 12 to a wound site. FIG. 3 is designed for use by a left-handed health care provider or for application to a wound site on the left side of a patient.

Figure 4:
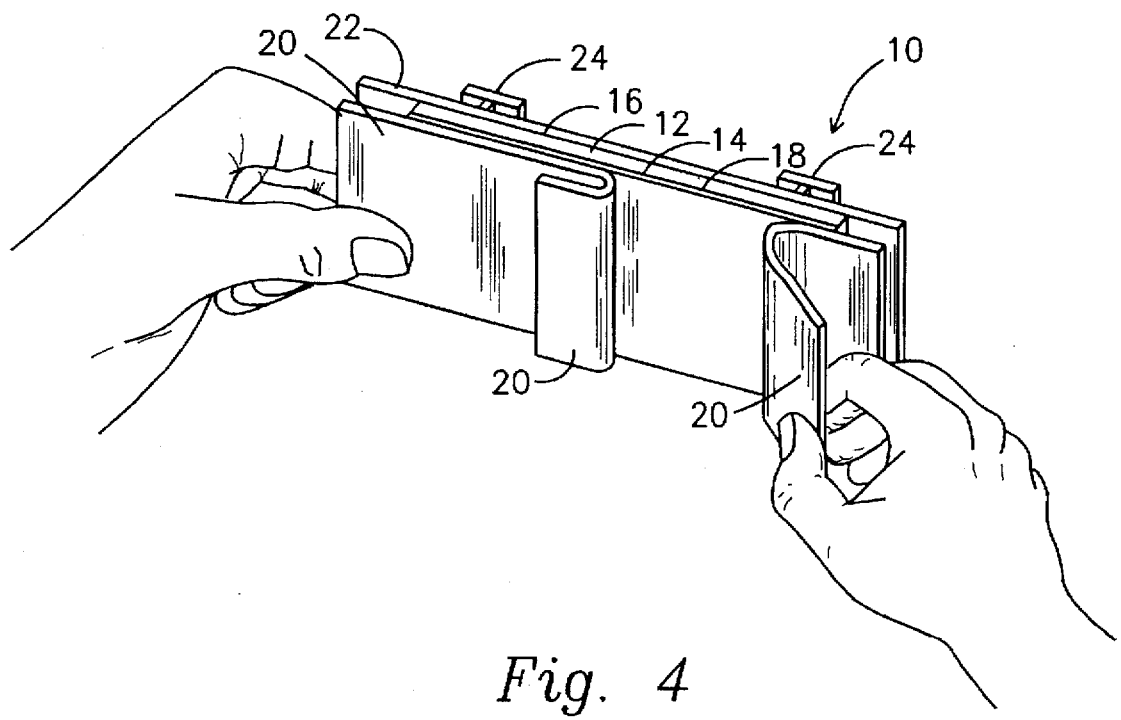
FIG. 4 is a side, elevational view demonstrating removal of the release from a wound dressing according to the present invention.

Referring again to the embodiment of the present invention shown in FIG. 3, in FIG. 4 the release layer 20 is removed by the user's grasping of end portion 20a with one hand 42 while at the same time grasping end portion 22b of the support layer 22 with the other hand 44. The release layer 20 can then be stripped of the wound dressing 10 without fear of removing the dressing layer 12 from the support layer 22. Subsequent to this removal of the release layer 20, the dressing layer 12 adhesive surface 18 can be placed on the appropriate location of the patient's skin, and the support layer 22 is readily removed by merely pulling the extended portion 24 of the support layer 22 with the user's hand and lifting the support layer 22 off of the dressing layer 12 which remains on the patient's skin by the downward force exerted on dressing layer 12 by delivery means 24.

Figure 5:
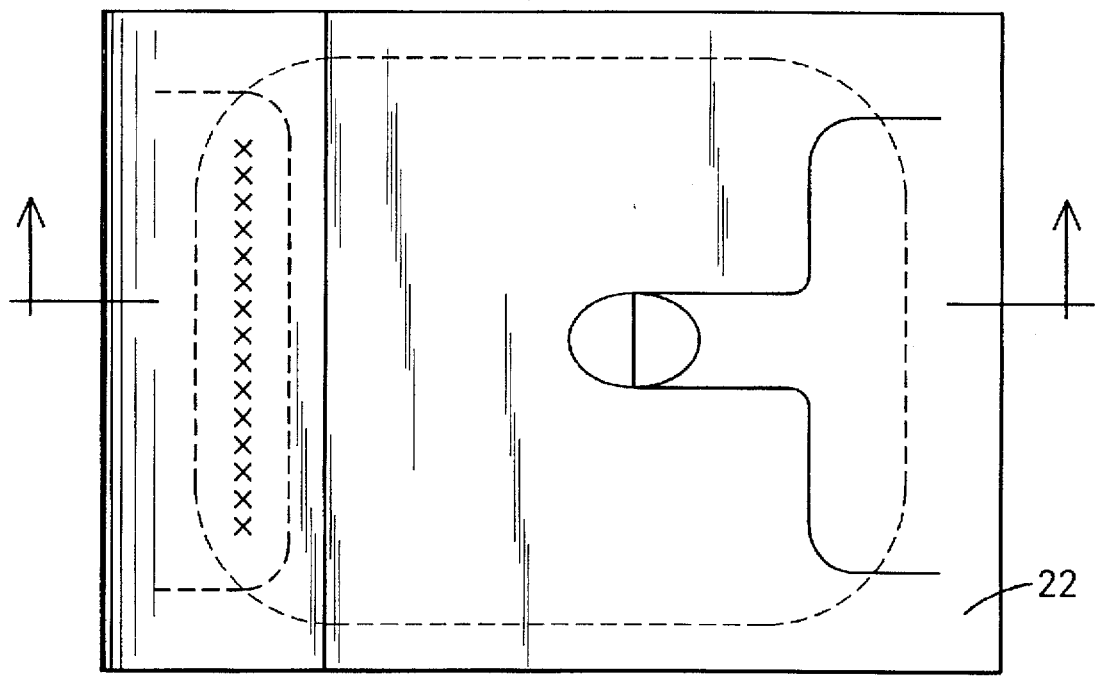
FIG. 5 is a top plan view of another embodiment of a wound dressing according to the present invention.

FIG. 5 is a further embodiment of the present invention. FIG. 5 is a dressing according to the present invention wherein the delivery means 24 forms an integral portion of support layer 22.

Figure 6:
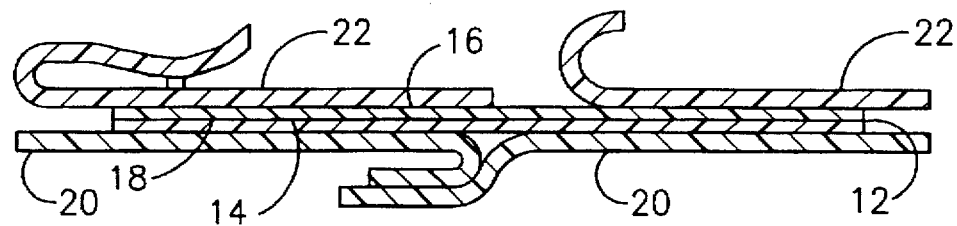
FIG. 6 is a side, cross-sectional view of the wound dressing shown in FIG. 5, taken along lines 2—2 thereof.

FIG. 6 is a side, cross-sectional view of the wound dressing shown in FIG. 5, taken along lines 2—2 thereof wherein the delivery means 24 forms an integral portion of support layer 22.

Figure 7:
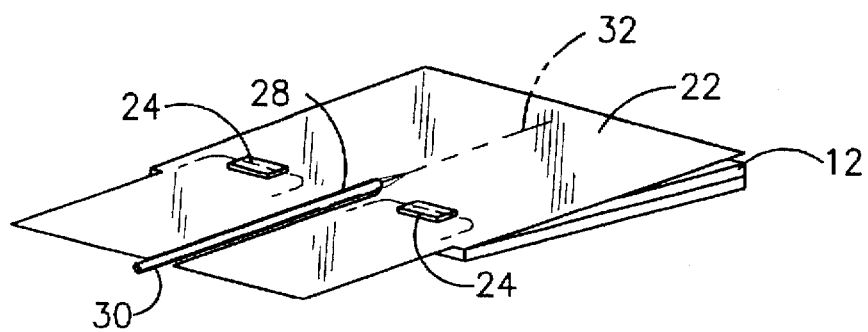
FIG. 7 is a top, perspective view of another wound dressing of the present invention including a fenestration for entry of a catheter tube.
Figure 8:
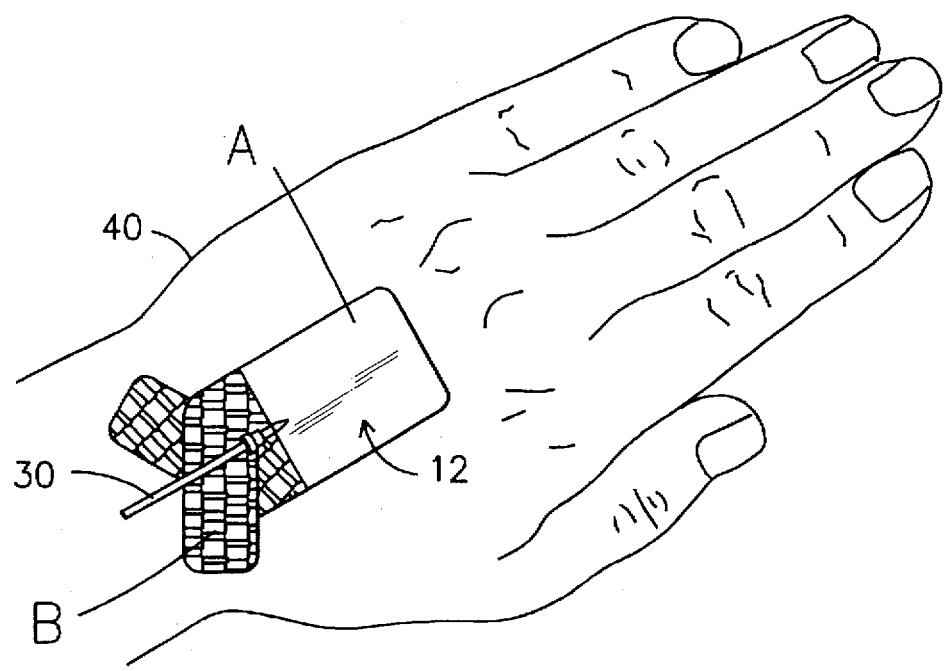
FIG. 8 is a top, elevational view of another wound dressing according to the present invention including a fenestration for application of a catheter tube applied to a patient's hand.

Another important embodiment of the present invention is shown in FIG. 7 and 8. Fenestration 28 has been cut through the dressing layer 12 as well as the support layer 22. Additionally, support layer 22 has also been cut in a line parallel to a catheter 30 which has previously been applied to a patient's skin. This cut line 32 thus permits the dressing itself to be fit over catheter 30 as it is initially being applied to the patient's skin. Delivery means 24 facilitates application of the dressing layer during removal of support layer 22. Dressing layer 12 can then be slightly twisted under the catheter 30 and removed in sections to provide a sealed dressing layer 12 around and under the catheter 30. This can be more readily seen with reference to FIG. 8.

Figure 9:
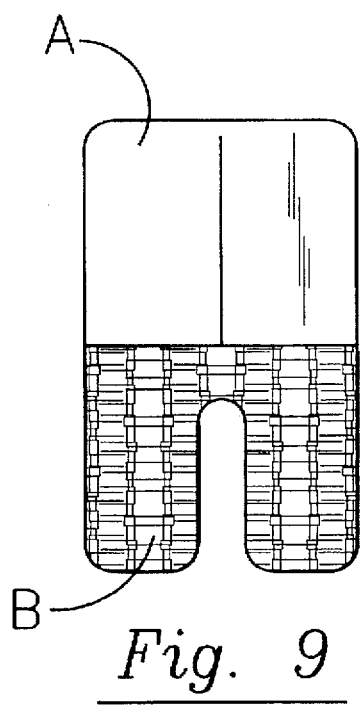
FIG. 9 is a top, elevational view of another wound dressing according to the present invention.

The embodiment shown in FIG. 8, however, includes a dressing layer 12 which is divided into two dressing areas A and B. In this embodiment dressing areas A and B can comprise different types of dressing layers in various combinations. In the embodiment shown in FIG. 8, for example, dressing area A comprises a film layer portion, while dressing area B, which includes two dressing layer portions divided by a fenestration means, includes a non-woven fabric or foam layer (i.e., a non-film layer). An absorbent material may be used, or a portion may be attached dressing area B for purposes of sealing off the puncture site where catheter 30 penetrates the skin 40. This provides securement and support for catheter 30, and protects the skin from pressure, abrasion and the like. This can be accomplished in a number of ways and in a number of variations. Thus, as shown in FIGS. 9–11, the configuration in which the dressing area A is a film layer and the dressing area B, including the fenestration, is a non-woven fabric area as in FIG. 8.

Figure 10:
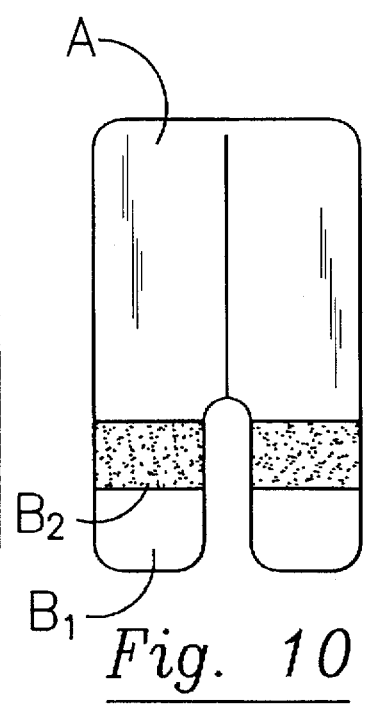
FIG. 10 is a top, elevational view of another wound dressing according to the present invention.
Figure 11:
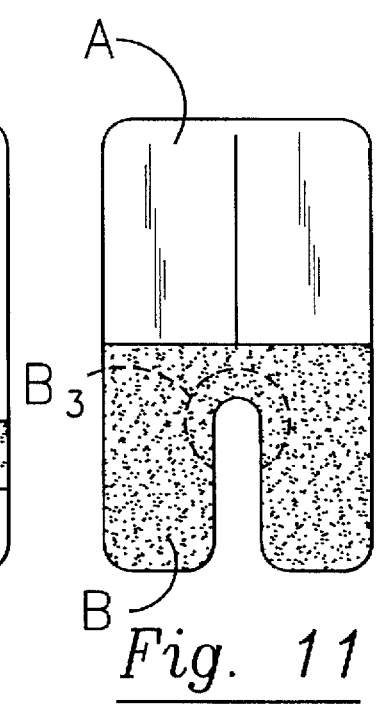
FIG. 11 is a top, elevational view of yet another wound dressing according to the present invention.

FIG. 10 shows a dressing area A which again comprises a film layer, while portions of dressing area B comprise a film layer ($B_1$) and a layer of polyurethane foam ($B_2$).

Finally, in FIG. 11, dressing area A again comprises a film layer, while dressing area B comprises a layer of polyurethane foam with an absorbent material attached to the underside thereof, as shown by broken line $B_3$.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. An improved medical dressing, comprising:
    a dressing layer having a first face and a second face, the first face having an adhesive coating on at least a portion thereof;
    a release layer covering the dressing layer in releasable contact with the adhesive face of the dressing layer;

a support layer covering the dressing layer in releasable contact with the second face of the dressing layer, the dressing layer having smaller surface dimension than the release layer and the support layer, the support layer having on at least one side thereof a U-shaped perforation therethrough, the perforation extending from an area adjacent an edge of the support layer and overlapping the smaller surface dimension of the dressing layer; and a delivery means for applying the dressing layer to a wound site during removal of the support layer, the delivery means pivotally mounted on a portion of the support layer adjacent the base of the U-shaped perforation.

2. The dressing of claim 1 wherein the delivery means protrudes over both sides of the base of the U-shaped perforation.

3. The dressing of claim 2 wherein the delivery means further comprises a portion of the support layer declining away from the plane of the support layer.

4. The dressing of claim 3 wherein the portion of the support layer which declines away from the plane of the support layer comprises a hinged handle.

5. The dressing of claim 1 wherein the dressing layer and the support layer are fenestrated along a path of intended catheter coverage, the support layer having at least one section.

6. An improved medical dressing, comprising:

a dressing layer having a first face and a second face, the first face having an adhesive coating on at least a portion thereof;

a release layer covering the dressing layer in releasable contact with the adhesive face of the dressing layer;

a support layer covering the dressing layer in releasable contact with the second face of the dressing layer, the dressing layer having smaller surface dimension than the release layer and the support letter, the support layer having on at least one side thereof a U-shaped perforation therethrough, the perforation extending from an area adjacent an edge of the support layer and overlapping the smaller surface dimension of the dressing layer; and a delivery means for applying the dressing layer to a wound site, the delivery means pivotally mounted on a portion of the support layer adjacent the base of the U-shaped perforation.

7. The dressing of claim 6 wherein the delivery means protrudes over both sides of the base of the U-shaped perforation.

8. The dressing of claim 7 wherein the delivery means further comprises a portion of the support layer declining away from the plane of the support layer.

9. The dressing of claim 8 wherein the portion of the support layer which declines away from the plane of the support layer comprises a hinged handle.

10. The dressing of claim 6 wherein the dressing layer and the support layer are fenestrated along a path of intended catheter coverage, the support layer having at least one section.

* * * * *